United States Patent
Burgisser

(10) Patent No.: US 7,073,531 B2
(45) Date of Patent: Jul. 11, 2006

(54) VALVE BLOCK

(75) Inventor: Ernst Burgisser, Rheinfelden (CH)

(73) Assignee: EPR Labautomation AG, Allschwil (CH)

( * ) Notice: Subject to any disclaimer, the term of this patent is extended or adjusted under 35 U.S.C. 154(b) by 239 days.

(21) Appl. No.: 10/481,803

(22) PCT Filed: Jun. 10, 2002

(86) PCT No.: PCT/CH02/00306

§ 371 (c)(1),
(2), (4) Date: Jan. 22, 2004

(87) PCT Pub. No.: WO03/001215

PCT Pub. Date: Jan. 3, 2003

(65) Prior Publication Data

US 2004/0112441 A1  Jun. 17, 2004

(30) Foreign Application Priority Data

Jun. 26, 2001 (CH) ..................... 1171/01

(51) Int. Cl.
*F17D 1/00* (2006.01)

(52) U.S. Cl. ................. 137/597; 137/613; 137/625.48; 422/103

(58) Field of Classification Search ................. 137/597, 137/625.48, 872, 613; 422/103
See application file for complete search history.

(56) References Cited

U.S. PATENT DOCUMENTS

| | | | | | |
|---|---|---|---|---|---|
| 2,857,082 | A | * | 10/1958 | Perkins | 141/238 |
| 2,904,070 | A | * | 9/1959 | Lynott | 137/883 |
| 3,652,228 | A | * | 3/1972 | Bernard | 137/625.48 |
| 5,137,698 | A | | 8/1992 | Ansorge et al. | |
| 5,538,694 | A | | 7/1996 | Delius | |
| 6,605,256 | B1 | * | 8/2003 | Guller et al. | 422/103 |

FOREIGN PATENT DOCUMENTS

WO   WO 98/57738   12/1998

* cited by examiner

*Primary Examiner*—Stephen M. Hepperle
(74) *Attorney, Agent, or Firm*—Rankin, Hill, Porter & Clark LLP

(57) ABSTRACT

A valve block (1) for a dosing device with an arrangement of piston pipettes (2) or other dosingdevices, includes, on its one face, a pattern of first mouths (15) to be aligned with the arrangement of piston pipettes (2) and, on the opposite face, second mouths (16) each respectively assigned to a first mouth (15). The valve block (1) also includes a plurality of channel systems (20) each with a main connector (23). The valve block (1) has a plurality of plates (10, 11, 12, 13) arranged in a stack. All plates define through holes (14), which are arranged in the pattern of the first mouths (15). At least a part of the plates (11, 12, 13) also have a channel system (20) with channels (21) connected with the main connector (23), wherein the channels (21) form a pattern, which is matched to the pattern of the through holes (14) and which is laterally displaced relative to this pattern. For optionally connecting the first mouths (15) with the corresponding second mouth (16) or with a selected channel system (20), the plate (11, 12 or 13) including the selected channel system is laterally displaced.

6 Claims, 2 Drawing Sheets

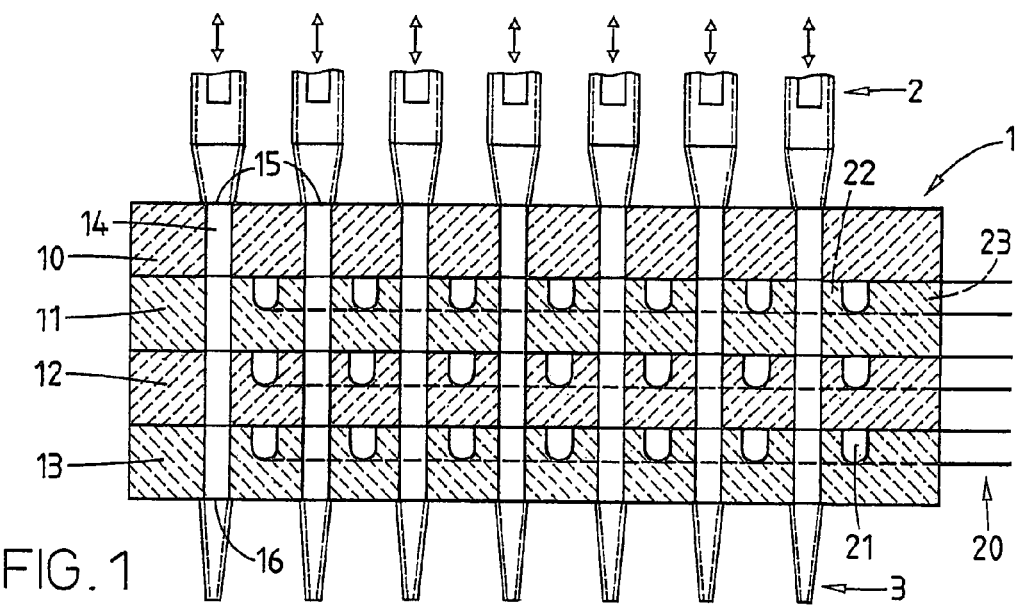

VALVE BLOCK

BACKGROUND OF THE INVENTION

1. Field of the Invention

The present invention is situated in the field of microanalytics and relates to a valve block for use in a dosing device for handling in parallel a large number of small liquid volumes, e.g., for simultaneously dosing small volumes of liquid into a plurality of cavities in a test plate or for extracting such volumes from the cavities.

2. Description of Related Art

In the publication EP-0363450 (or U.S. Pat. No. 5,193,403, Bürgisser) a dosing device of the named kind is described. The EP '450 dosing device comprises a plurality of piston pipettes or of similar dosing means, which are equipped for drawing in or expelling liquid through a distal end in an exactly dosed manner. The device further comprises a valve plate having two principle surfaces of which one is oriented towards the distal ends of the pipettes and is pressed against these, for example, by means of a spring force.

The valve plate comprises a pattern or grid of through holes (extending from one to the other principle surface of the valve plate), which pattern is adapted to the arrangement of piston pipettes such that each one of the distal pipette ends can be aligned with one of the through holes. On the other principle surface of the valve plate, hollow dosing tips are connected to the mouths of the through holes. The valve plate further comprises two channel systems, each of which comprises a main connector and a plurality of openings in the one valve plate surface facing the distal pipette ends and being connected with the main connector through channels. The mouths of each channel system also form a pattern, which is adapted to the arrangement of the pipettes. Of the channel systems, for example, one is connected to a source of liquid via the main connector and the other one to a discharge outlet.

By displacing the pipette arrangement relative to the valve plate, the distal ends of the piston pipettes are optionally connected with the through holes or with the mouths of one or the other of the channel systems, such making a plurality of dosing functions possible.

The dosing device briefly described above is simple and robust and it can be operated at satisfactory speeds. Because, however, for every channel system a mouth grid defined by the grid of through holes has to be provided in the plate surface facing the pipettes and has to be accommodated within the grid of through holes, the fineness of the grid of through holes limits the number of channel systems. The same limitation also applies in view of manufacturing technology, because the valve plate essentially is manufactured as a single piece.

For the described valve plate, increasing the number of possible connections to different sources of liquid, i.e. increasing the number of channel systems, makes it necessary to increase the distances between the through holes in the valve plate and, as a result, also to use a coarser grid for the pipette arrangement. This, however, signifies that cavities of test plates of a fine cavity grid cannot be served in parallel, which in turn leads to an undesirable increase of time necessary for the operation.

SUMMARY OF THE INVENTION

An object of the invention is to create a valve block for a dosing device, as it is briefly described above, wherein the valve block is capable of being manufactured in a simple way, independent of the number of the channel systems it is to comprise, wherein the valve block furthermore is capable of being realized in a simple manner even with very small grid dimensions (distances between through holes) and wherein in this valve block the grid dimensions in no way limit the possible number of channel systems.

The valve block according to the invention comprises modularly assembled plates. The valve block comprises a connector plate and a plurality of advantageously identical channel plates, each of which respectively represents one of the channel systems. The plates are arranged in a stack adjacent to one another and such that they can be displaced relative to one another within limits. The connector plate is directed towards the distal ends of an arrangement of piston pipettes or other dosing means and comprises a plurality of through holes, each one of which is to be aligned with one distal pipette end. The channel plates also comprise through holes, wherein the through holes of the connector plate and of the channel plates are arranged to be aligned with one another, i.e. the through holes of each plate are arranged in the same pattern or grid. Every channel plate further comprises a channel system that is open to at least one side of the plate, and that is matched to the grid of the through holes, but is arranged laterally displaced relative to the grid of the through holes. The channel system comprises at least one main connector that is arranged advantageously at a narrow side of the plate.

Within the stack, the channel plates are arranged displaceable relative to one another and relative to the connector plate such that each channel plate is essentially able to have two positions: a first position, in which its through holes are aligned with the through holes of the connector plate, and a second position, in which its channel system is aligned with the through holes of the connector plate.

By positioning the channel plates relative to each other in a corresponding manner, it becomes possible in a very simple manner to connect the distal ends of the piston pipettes either with the dosing tips on the opposite side of the valve block or with a selected one of the channel systems or its main connector, respectively. It remains to be demonstrated that, for connecting the distal ends of the pipettes with the main connector of a predefined channel plate, it is sufficient to bring this predefined channel plate into the above named second position and to leave all other channel plates in the first position.

The connector plate and the channel plates of the valve block in accordance with the invention consist of a material that constitutes surfaces (if so required correspondingly machined), which are capable, on the one hand, to seal against one another and, on the other hand, to be displaced relative to one another while still sealing. Furthermore, the material, of course, must not be corrosively affected by the liquids utilized. From the field of valve technology, in particular from the very widespread single lever mixers it is known that, for applications of this kind, ceramic materials are advantageously utilized.

BRIEF DESCRIPTION OF THE DRAWINGS

The valve block according to the invention is described in more detail on the basis of the following Figures, wherein:

FIGS. 1 to 3 show an exemplary embodiment of the valve block in accordance with the invention in cross section and with different positions of channel plates;

DETAILED DESCRIPTION OF THE PREFERRED EMBODIMENTS

Figure 4:
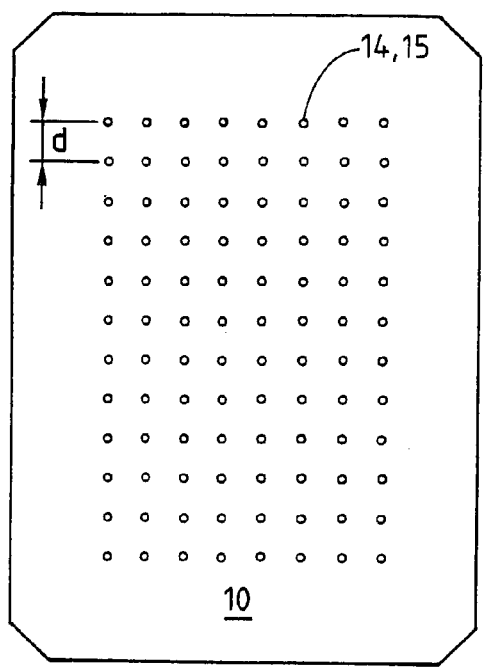
FIG. 4 shows the outer surface of the connector plate of an exemplary embodiment of the valve block according to the invention.

FIG. 1 illustrates a very schematic and not complete cross section through a dosing device, as it has been described further above. Of the dosing device are illustrated: a valve block 1 according to the invention, an arrangement of dosing means (e.g., dosing pipettes 2) arranged on the one face of the valve block 1 and an arrangement of dosing tips 3 arranged on the opposite face of the valve block 1. The valve block 1 comprises a connector plate 10 and adjacent to the connector plate 10 a first, second and third (outermost) channel plate 11, 12, and 13, wherein the plates with the help of suitable means (not illustrated) are held together in a stack such that the connector plate 10 forms the one face of the stack and the outermost channel plate 13 the other face.

The connector plate 10 and the channel plates 11, 12, and 13 comprise through holes 14 arranged in an identical, advantageously regular pattern (grid), which pattern is matched to the arrangement of the piston pipettes. On the faces of the stack of plates, therefore on the connector plate 10, and on the outermost channel plate 13 these through holes have first mouths 15 and second mouths 16, to which are connected piston pipettes 2 or other suitable dosing means, or the dosing tips or other suitable connection means, respectively.

In addition to the pattern of through holes, each one of the channel plates comprises a channel system 20. The channel system of each channel plate is designed in the same manner to connect mouths of a mouth, pattern with at least one main connector, wherein the mouth pattern is the same as the pattern of through holes, but is laterally displaced relative to the latter. If, for example, the through holes are arranged in straight rows, then the channels of the channel system run parallel to these rows and with a constant distance or spacing to the rows. Furthermore, advantageously outside of the pattern of through holes, the channel systems comprises collecting channels, which connect the channels with the at least one main connector.

FIG. 1 shows in cross section channel plates comprising channels 21 arranged between rows of through holes 14. A collecting channel 22 running parallel to the intersecting plane is indicated with discontinuous or dashed lines. Indicated in the same manner is a main connector 23. The channels 21 are arranged, e.g., centrically between the rows of through holes 14, so that a lateral displacement of two adjacent plates by half the grid dimension results in switching between a configuration in which the through holes 14 of the two plates are aligned and a configuration in which the channels of the one plate are aligned with the through holes of the other plate.

The channel systems 20 of the channel plates 11, 12, and 13 in accordance with FIG. 1 comprise a depth, which is smaller than the thickness of the plate (trough-shaped channels). Therefore, the channels in the stack of plates are closed on one side by an adjacent plate. It is also possible to give the channels a depth that is the same as the thickness of the plate (slot-shaped channels). Slot-shaped channels are closed in the stack of plates by two adjacent plates, one on each side. In the case of the channel plates comprising slot shaped channels, a further connector plate has to be arranged on the face of the valve block opposite the connector plate 10.

The plates 10, 11, 12, 13, which together form the valve block 1 according to the invention, are advantageously formed from a ceramic material, for example, of aluminium oxide.

As shown in FIG. 1, it is advantageous to design all the channel plates 11, 12 and 13 to be identical, which keeps the price of the valve block low. If the channels are trough-shaped, it is obviously also possible to utilise a channel plate as a connector plate 10, wherein the channels of this plate do not have any functional significance.

The valve block 1 is held, for example, between two holding plates correspondingly perforated for the first and second mouths and which are, for example, made of steel. For displacing individual ones of the channel plates 11, 12, 13 within the valve block 1, on two sides of the stack of plates corresponding servo-motors are affixed, which when correspondingly driven act on one of the channel plates in a pushing manner.

In FIG. 1 the dosing device is represented in a condition in which the piston pipettes 2 are connected with the dosing tips 3 by the through holes 14 of all plates 10, 11, 12, 13 being aligned to one another. In FIG. 2, which only illustrates the valve block 1, the piston pipettes 2 are connected with the channel system of the third channel plate 13 by the through holes 14 of the connector plate 10 and the first two channel plates 11 and 12, which through holes are aligned with each other, while the third plate is displaced. In FIG. 3, which also only illustrates the valve block 1, the piston pipettes 2 are connected with the channel system of the first channel plate 11 through the through holes 14 of the connector plate 10.

A comparison of FIGS. 1, 2 and 3 demonstrates that, for a changeover of the valve block 1 from a condition in which the first and second mouths 15 and 16 are connected with one another to a condition in which the first mouths 15 are connected with a selected one of the channel systems, a displacement of the corresponding channel plate by half a grid dimension is sufficient (FIG. 2: third channel plate 13, FIG. 3: first channel plate 11).

FIG. 4, as a plan view from above, illustrates an exemplary embodiment of a connector plate 10. The through holes 14 or the first mouths 15, respectively, are arranged in rows with a spacing d. The pattern of the through holes corresponds, for example, to the cavity pattern of a standardized micro test plate (comprising 96, 384 or 1536 cavities).

Figure 5:
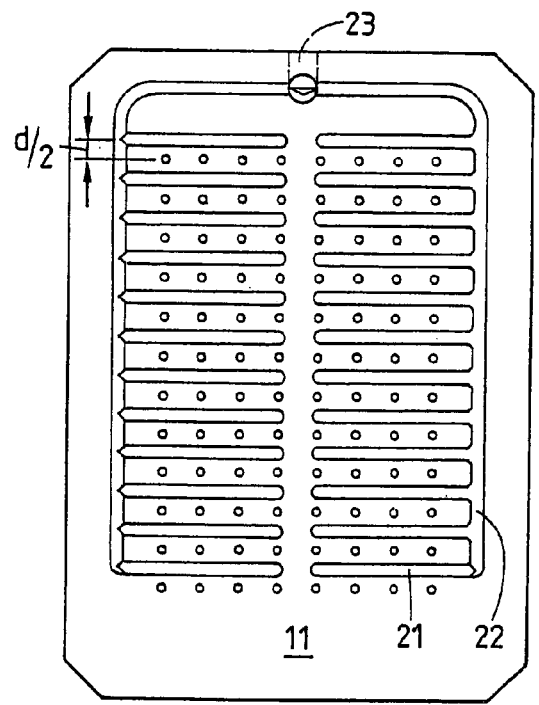
FIG. 5 shows, viewed from above, a channel plate of the same embodiment of the valve block in accordance with the invention.

FIG. 5 illustrates a channel plate 11, which together with the connector plate 10 of FIG. 4 can be utilized in a valve block in accordance with the invention. The channel plate 11 comprises channels 21, which run centrically between the rows of through holes and therefore have a distance of d/2 from these rows. The channels 21 run into collecting channels 22, which extend or run outside of the pattern of through holes and which for their part lead to the main connector 23.

Figure 6:
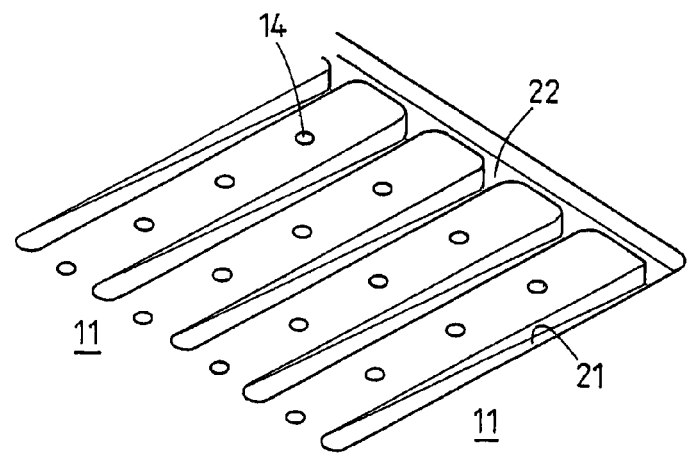
FIG. 6 shows a detail of the channels of the channel plate according to FIG. 5.

FIG. 6 in a detailed three dimensional view illustrates the channels 21 of the channel plate 11 in accordance with FIG. 5. These channels 21 run centrically between the rows of through holes 14 and are trough-shaped, as is also depicted in the FIGS. 1 to 3. In order to guarantee a regular distribution of the liquid to all through holes connected with the channels 21, the channels 21 advantageously are designed such that their cross section gets larger towards their outlet into a collecting channel 22. This is implemented, for example, as shown in FIG. 6, by an increasing depth of the trough-shaped channels, i.e., by having a bottom wall of the trough-shaped channels 21 slope toward the collecting channel 22.

The invention claimed is:

1. A valve block for a dosing device with an arrangement of dosing means, said valve block comprising, on a first face, a first pattern of first mouths (15) to be aligned with the dosing means and, on a second face opposite the first face, second mouths (16) each corresponding to one of the first mouths and a plurality of channel systems (20) each comprising at least one main connector (23), wherein the valve block (1) comprises a plurality of plates (10, 11, 12, 13) superimposed in a stack and each of said plates defining a plurality of through holes (14) arranged in the first pattern, the plates being laterally displaceable relative to each other for selectively connecting the first mouths (15) with either a second mouth (16) each or with one of the channel systems, wherein an outermost plate in the stack is a connector plate (10) and all other plates are identical channel plates (11, 12, 13), wherein the channel plates, in addition to the through holes (14), comprise on a first face a channel system (20) with channels (21) running into a main connector (23) arranged on a narrow side of the channel plate, wherein all channels are trough-shaped and are closed by a second face of a superimposed plate and wherein the channels (21) are arranged in a second pattern, which is matched to the first pattern and laterally displaced relative to the first pattern.

2. The valve block in accordance with claim 1, wherein the through holes (14) are arranged in rows and the channels (21) run between the rows and with a constant distance from the rows.

3. The valve block according to claim 1, wherein the channel systems (20) further comprise collecting channels (22) running outside of the pattern of through holes (14).

4. The valve block according to claim 1, wherein the connector plate (10) is identical to the channel plates (11, 12, 13).

5. The valve block according to claim 1, wherein a cross section of the channels (21) gets larger towards a channel outlet into a collecting channel (22) or into the main connector (23).

6. The valve block according to claim 1, wherein the plates (10, 11, 12, 13) are formed from a ceramic material.

* * * * *